Aug. 13, 1935. J. H. NICOLAS Plant Pat. 131
ROSE
Filed March 13, 1935
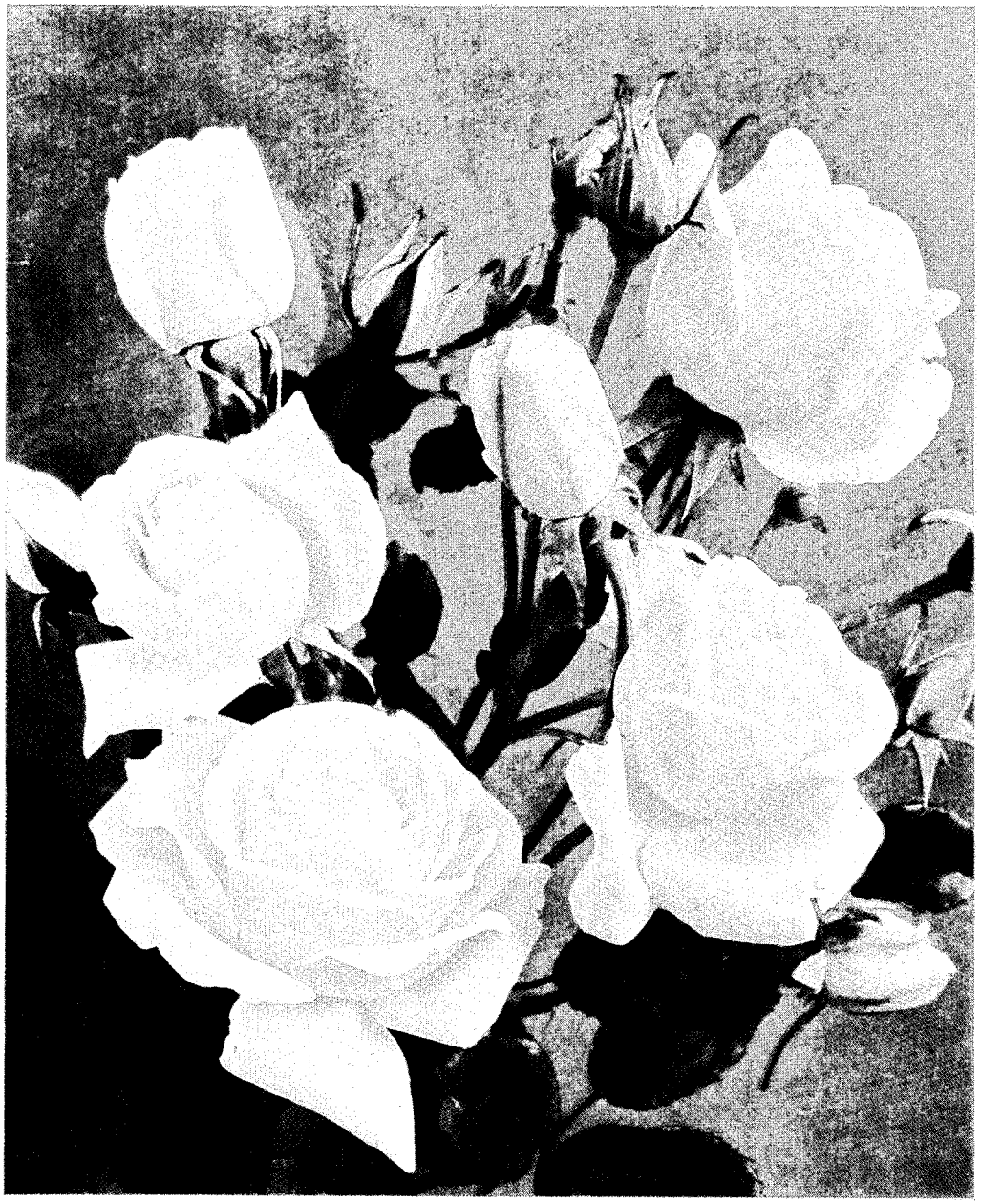
Inventor
Jean H. Nicolas
By Robb & Robb
Attorneys.

Patented Aug. 13, 1935

UNITED STATES PATENT OFFICE

131

ROSE

Jean H. Nicolas, Newark, N. Y., assignor to Jackson & Perkins Company, Newark, N. Y.

Application March 13, 1935, Serial No. 10,945

1 Claim. (Cl. 47—61)

This invention relates to a new and distinct variety of rose plant, having as its objective the production of a rose of the type and quality of the well known "Rev. F. Page Roberts", but borne on a better plant possessing more winter hardiness.

In attaining this new product, it is found that the plant has retained much of the characteristics of the polyantha hybrid "Echo", its seed parent, while its blooms can be grown to the size and type of its pollen parent "Rev. F. Page Roberts".

Another feature of importance which marks its distinction from others of its class is the fact that the main shoots from the base will bloom in very large clusters of thirty-five and more blooms. The succeeding laterals will have solitary blooms on them or will carry groups of up to as many as five buds which can be disbudded to obtain large exhibition blooms.

For general purposes, it is a bedding variety of very abundant floriferousness.

The plant is of extreme hardiness, having gone through several normal winters of New York State uninjured and a recent extreme winter when the temperature reached 28° below zero, with but very little freeze back.

It may also be noted that as a hardy polyantha variety, the bloom is of a new type and color combination as hereinafter described, and in the year 1934, its value as a new variety was attested by the award of the Gold Medal of the American Rose Society for one of the most distinct novelties of that year, and by the fact that it was also selected on competition to commemorate the Centennial of the City of Rochester.

This rose has been asexually reproduced and its characteristics have been found to be fixed.

As a further convenient means of identification, the following detailed description is given:

Parentage:

Seedling.

*Seed parent.*—"Echo".

*Pollen parent.*—"Rev. F. Page Roberts".

Classification:

*Botanic.*—Hybrid polyantha.

*Commercial.*—Hybrid tea.

*Flower*

Blooming habit:

Continuous all season.

Bud:

*Size.*—Medium.

*Form.*—Short; pointed; unaffected by wet or hot weather.

**Color.*—When sepals first divide and petals begin to unfurl light yellow with carmine markings. When half blown inside of petals cream and pearl yellow at base; reverse of petals carmine.

*Sepals.*—Smooth edge; stand up.

*Calyx.*—Shape—funnel; size—small; aspect—smooth; odor when rubbed—none.

*Peduncle.*—Length—medium; aspect—smooth; color—light green; strength—slender.

*Opening.*—Opens well; is not affected by adverse conditions.

Bloom:

*Size.*—Medium, small, varying according to number in cluster; may be grown to 3½" to 4" by disbudding.

*Borne.*—Singly and in clusters; in clusters flat and irregular.

*Stems.*—Medium, weak.

*Form.*—When first open high center, globular.

*Permanence.*—Retains its form to the end.

*Petalage.*—Very double (many petals and stamens hidden). Number of petals under normal conditions 40 to 50. Color variable according to weather; the carmine markings are more intense in dry weather and the yellow deeper in moist weather. The general tonality is darker in autumn. Center of flower pearl and light yellow. Outer petals carmine. Base of petals (aiglet) yellow. Inside of petals pearl and light yellow. Reverse of petals carmine with cream edges and yellow base. General tonality from a distance pearl.

*Variegations.*—None.

*Discoloration.*—General tonality at end of first day same; second and third days carmine markings intensify with age.

Petals:

*Texture.*—Thick; unaffected by wet or hot weather.

*Appearance.*—Inside satiny. Outside satiny.

*Form.*—Round.

*Arrangement.*—Irregular; sometimes quartered. Petaloids in center; many, small.

*Persistence.*—Hang on and dry.

*Fragrance.*—Moderate.

*Nature.*—Tea (average hybrid tea) scent.

*Lasting quality.*—On plant very long; as cut flower very long.

Genital organs:

*Stamens, anthers.*—Few. Color—white. Arrangement—mixed with petaloids.

*Stamens, filaments (threads).* Short. Color—white.

*Pollen.*—Lemon yellow.

*Styles.*—Bunched, uneven length. Short, long, heavy.

*Stigmas.*—Color—white.

*Ovaries.*—Some protruding from calyx.

Fruit:

Variety is generally sterile with its own pollen or any other pollen.

(* Gravereaux color system)

*Plant*

Form:
Bush.
Growth:
Very vigorous, branching, sprawly.
Foliage:
Five or seven leaflets.
*Size.*—Large.
*Quantity.*—Abundant.
*Color.*—New foliage—upper side bronzy; under side reddish. Old foliage—upper side normal green; under side light green.
*Shape.*—Oval pointed.
*Texture.*—Upper side leathery, smooth; under side smooth.
*Ribs and veins.*—Ordinary.
*Edge.*—Serrated (saw toothed).
*Serrations.*—Single, small.
*Leaf stem or rachis.*—Color—green. Under side—smooth.
*Stipules.*—Medium, smooth.
*Disease resistance.*—Susceptible to mildew.
Wood:
*New wood.*—Color reddish, brown. Bark—smooth.
*Old wood.*—Color green. Bark—smooth.
Thorns:
*Thorns.*—Quantity—on main stalks from base few; on laterals from stalks few. Form—broad base; medium; straight. Color when young—green. Position—irregular.
*Prickles.*—Quantity—on main stalks none; on laterals none.
*Short needles.*—Quantity—on main stalks none; on laterals none.
I claim:
A new and distinct rose plant as shown and described characterized importantly by the great hardiness of the plant and the new type and color combination of abundant blooms in a hardy polyantha variety, susceptible of being grown to exhibition hybrid tea size and quality.

JEAN H. NICOLAS.